United States Patent

Kim et al.

[11] Patent Number: 5,500,400
[45] Date of Patent: Mar. 19, 1996

[54] CATALYST FOR PRODUCING 1,1,1,2-TETRAFLUOROETHANE AND METHOD FOR PREPARING THE SAME

[75] Inventors: Hoon Sik Kim; Byung Gwon Lee; Honggon Kim; Kun You Park, all of Seoul, Rep. of Korea

[73] Assignee: Korea Institute of Science and Technology, Seoul, Rep. of Korea

[21] Appl. No.: 302,636

[22] Filed: Sep. 8, 1994

[30] Foreign Application Priority Data

Dec. 9, 1993 [KR] Rep. of Korea ............... 1993-27091

[51] Int. Cl.$^6$ ........................................ B01J 23/26
[52] U.S. Cl. ..................... 502/306; 502/168; 502/169; 502/170; 502/228; 502/320
[58] Field of Search .................... 570/168, 170, 570/169, 165; 502/228, 320, 306

[56] References Cited

U.S. PATENT DOCUMENTS

| | | |
|---|---|---|
| 3,755,477 | 8/1973 | Firth et al. . |
| 4,129,603 | 12/1978 | Bell ................................... 260/653 |
| 4,139,568 | 2/1979 | Baugh, Jr. et al. ................ 570/165 |
| 4,153,675 | 6/1979 | Potter ................................ 260/653 |
| 4,547,483 | 10/1985 | Müller et al. . |
| 5,155,082 | 10/1992 | Tung et al. . |
| 5,281,568 | 1/1994 | Scott et al. . |
| 5,321,170 | 6/1994 | Corbin et al. . |

FOREIGN PATENT DOCUMENTS

| | | | |
|---|---|---|---|
| 1117145 | 9/1978 | Canada ........................... 260/658.2 |
| 0328127 | 2/1989 | European Pat. Off. ......... C07C 17/20 |
| 2932934 | 8/1979 | Germany ....................... C07C 19/08 |
| 53-105404 | 9/1978 | Japan ............................. C07C 19/08 |

*Primary Examiner*—Asok Pal
*Attorney, Agent, or Firm*—Darby & Darby

[57] ABSTRACT

There are a catalyst for producing 1,1,1,2-tetrafluoroethane represented as $Cr_aL_bM_cO_xF_y$, wherein L is Mg or Ca; M is one element selected from a group consisting of Ce, Ni, Zn, and Al; and each value of a, b, c, x and y are all between 0 and 2, and a method for preparing the same comprising the steps of: producing an admixture of a composition comprising chromium hydroxide hydrate and magnesium chloride or calcium chloride in a weight ratio of Cr to Mg or Ca ranging from 1:0.3 to 1:10 with an aqueous metal salt solution; reacting the admixture with an aqueous HF solution to give a paste; and sintering the paste.

6 Claims, No Drawings

CATALYST FOR PRODUCING 1,1,1,2-TETRAFLUOROETHANE AND METHOD FOR PREPARING THE SAME

BACKGROUND OF THE INVENTION

1. Field of the Invention

The present invention relates, in general, to a catalyst for the production of 1,1,1,2-tetrafluoroethane ($CF_3CH_2F$: hereinafter referred to as "HFC-134a") and, more particularly, to a catalyst for the partial fluorination of 1,1,1-trifluoro-2-chloroethane ($CF_3CH_2Cl$: hereinafter referred to as "HCFC-133a") to HFC-134a, significantly improved in durability, selectivity and activity. Also, the present invention relates to a method for the preparation of the catalyst.

2. Description of the Prior Art

Dichlorodifluoromethane ($CCl_2F_2$: hereinafter referred to as "CFC-12") has been one of the most important cooling agents utilized extensively in refrigerators, automobile cooling systems, and various other related industries because it is harmless to the human body and superior in thermodynamic physical properties. However, intensive research and observation has revealed that CFC-12 is a main substance that destroys the ozone layer in the stratosphere. According to the Montreal protocol internationally agreed in 1987, it is prescribed that CFC-12 should be prohibited from production and use starting from 1996.

HFC-134a, is another cooling agent that has similar physical properties to CFC-12. But, it does little damages to the ozone layer and has a much less influence to the earth's greenhouse effect. Accordingly, as the best substituent for CFC-12, it attracts attention with keen interest.

HFC-134a may be produced by reacting various $C_2$ compounds with HF, for example, by reacting HCFC-133a with HF as shown in the following reaction formula:

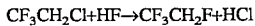

$$CF_3CH_2Cl+HF \rightarrow CF_3CH_2F+HCl$$

However, it is known that the substitution of fluorine for chlorine in HCFC-133a is a very difficult reaction. Thus, an effective catalyst is required to promote this reaction. As previously known, chromium oxide (III) ($Cr_2O_3$) is an effective catalyst for the partial fluorination of HCFC-133a and superior to other catalysts. In many a patent, techniques for the preparation of the chromium oxide are disclosed.

Chromium oxide (III) catalysts developed thus far, however, include many disadvantages that need to be improved, such as catalyst life span and selectivity. For example, since the partial fluorination reaction proceeds at high temperatures, e.g. above 350° C., an organic material, a reactant for the partial fluorination reaction, is discomposed to deposit carbons on the catalyst. As a result, the catalyst is deactivated at a rapid rate. In order to retard the deactivation rate of the catalyst, a process of providing oxygen together with the reactants at a constant ratio is disclosed in many patents, for example, European Patent No. 0 328 127 and German Patent No. 2932934. However, this process is not a basic solution for preventing the deactivation of the catalyst. In addition, the provided oxygen oxidizes the HCl resulting from the partial fluorination reaction to generate a chlorine gas which, in turn, reacts with the reactants to yield many by-products which make the separation and filtration of HFC-134a difficult. Of those by-products, particularly $CF_2CHCl$ (hereinafter referred to as "HCFC-1122") has a boiling point almost identical to that of HFC-134a, thus it is extremely difficult to separate HFC-134a from the by-products.

Chromium oxide, used as a catalyst for the fluorination, may be produced from a variety of chromium compounds, and is used alone or in an active carbon-supported or alumina-supported form.

Thus far, many methods for preparing the chromium oxide catalyst have been developed and disclosed in many patents. For example, in Japanese Patent Laid-Open Publication No. 53-105404, U.S. Pat. No. 4,153,675 and Canadian Patent No. 1117145, a process comprising treating a chromium compound (III), such as chromium chloride and chromium nitrate, with ammonia to give chromium hydroxide and sintering it at 200° to 500° C. is disclosed. Another process comprising pyrolyzing ammonium dichromate at 500° to 650° C. is suggested in European Patent Laid-Open Publication No. 0313061.

For the chromium oxide catalyst to be active in the fluorination reaction, conventionally, it is completely dried at 400° C. for 5 to 10 hours under nitrogen gas and then pre-treated with HF at 200° to 400° C. for 1 to 10 hours, prior to being used in the fluorination reaction. The pretreatment with HF is to change a part of the chromium oxide catalyst into a catalytic form of chrome oxyfluoride which is believed to be effective in the fluorination reaction. During this pretreatment, water is produced as a by-product as shown in the following reaction formula:

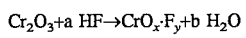

$$Cr_2O_3 + a\ HF \rightarrow CrO_x \cdot F_y + b\ H_2O$$

The water by-produced gives rise to significantly increasing the ability of the coexisting HCl and HF in a reactor to corrode the equipment including the reactor, having a serious effect on the durability of the equipment. In addition, additional equipment is required to eliminate the water during the separation of HFC-134a, the final product, therefore, making the overall production procedure for HFC-134a complicated. Furthermore, when unreacted reactants are recovered to be reused, incomplete removal of water therefrom is the main factor that degrades the activity and durability of the catalyst.

U.S. Pat. No. 4,129,603 discloses that chromium hydroxide is treated in steam, changed into a catalytic form of chrome oxyfluoride, and then used in production of HFC-134a. However, the selectivity of this catalyst is merely in the range of 91 to 95%. In addition, since HCFC-1122, which is hard to separate from the product due to its similar boiling point, is by-produced in a large quantity, there is the disadvantage that an additional reactor is necessary to remove it.

Germany Patent No. 29 32 934 suggests the use of chromium fluoride or chrome oxyfluoride as a catalyst for the partial fluorination reaction. At a reaction temperature of 400° C. and at a mole ratio of 7.7, early production yield of HFC-134a by this catalyst is only 26%. After reacting for 44 hours without supply of oxygen, the catalyst shows activity of just 22%. In addition, since oxygen need to be continuously supplied to reactants, the reaction is likely to produce by-products which makes the separation of HFC-134a more difficult.

European Patent No. 0328127 shows that a metal catalyst impregnated in alumina is effective for the production of HFC-134a. In this patent, the reported advantage of using this catalyst in the HFC-134a production process does not result in an increase of by-products compared to the case where chromium oxide catalyst is used, even during concomitant supply of reactants and oxygen. But, the selectivity of the catalyst for HFC-134a is at best 93.7% and at worst 55.2%.

SUMMARY OF THE INVENTION

The object of the present invention is to provide a catalyst for the production of 1,1,1,2-tetrafluoroethane, superior in selectivity and durability.

It is another object of the present invention to provide a catalyst for the production of 1,1,1,2-tetrafluoroethane, capable of maintaining its activity even after being used for a long period of time.

It is a further object of the present invention to provide a catalyst for the production of 1,1,1,2-tetrafluoroethane which can be used with ease because an additional pretreatment with HF solution is unnecessary prior to its use in the production of HFC-134a thereby.

It is still an additional object of the present invention to provide a method for the preparation of the catalyst, advantageous from an economic point of view.

The catalyst, in accordance with the present invention, can be prepared by a method comprising the steps of: producing an admixture of a composition comprising chromium hydroxide hydrate and chloride magnesium or calcium chloride in a ratio of Cr to Mg or Ca ranging from 1:0.3 to 1:10 with an aqueous metal salt solution selected from a group consisting of cerium chloride, zinc chloride, nickel chloride and aluminum chloride; reacting the admixture with an aqueous HF solution to give a paste; and sintering the paste.

The catalyst for the production of HFC-134a prepared by the method of the present invention has a composition as shown in the following empirical formula:

$$Cr_a L_B M_c O_x F_y$$

wherein L is Mg or Ca; M is one selected from a group consisting of Ca, Ni, Zn, and Al; and each value of a, b, c, x and y are all between 0 and 2.

These and other objects and advantages of the present invention will become more apparent in the following description.

DETAILED DESCRIPTION OF THE INVENTION

For the preparation of the catalyst according to the present invention, an aqueous chromium oxide solution is added with ethanol and refluxed under heat, to give a chromium hydroxide hydrate. To this chromium hydroxide hydrate, magnesium chloride or calcium chloride is added in a predetermined weight ratio and then mixed with an aqueous metal salt solution. Subsequently, the mixture is added with an aqueous HF solution. After the reaction proceeds at room temperature to 80° C. for 1 hour, filtration and drying steps are carried out to give a paste. The paste is subjected to sintering at 300° to 450° C. for 3 to 10 hours, to give the catalyst.

In the catalyst of the present invention, the weight ratio of Cr to Mg or Ca is suitably present in the range of 1:0.3 to 1:10 and preferably 1:1 to 1:4.

Based on the weight of the Cr, the metal component of the aqueous metal salt solution should not exceed 5% by weight and preferably less than 2% by weight. In the present invention, an aqueous solution of cerium chloride, zinc chloride, nickel chloride or aluminum chloride may be used.

The aqueous HF solution used in the present invention is 30–50% HF solution.

X-ray diffraction analysis of the catalyst provided by the present invention reveals that it is not present in a form of $CrF_3$ which has such characteristic peaks as 2θ=18.90, 21.68, 34.74, 48.52, 69.68, 69.84, or $MgF_2$ which has such characteristic peaks as 2θ=3.276, 2.230, 1.172, but in a catalytic form of $Cr_a L_b M_c O_x F_y$, wherein L is Mg or Ca; M is one element selected from a group consisting of Ce, Ni, Zn, and Al; and each value of a, b, c, x and y are all between 0 and 2.

Herein, the terms "change rate of HCFC-133a" and "selectivity for HFC-134a" are defined as follows:

$$\text{Change rate (\%)} = \frac{\text{amount of HCFC-133a reacted}}{\text{amount of HCFC-133a supplied}} \times 100$$

$$\text{Selectivity (\%)} = \frac{\text{amount of HFC-134a produced}}{\text{amount of HCFC-133a reacted}} \times 100$$

As described hereinbefore, since the method according to the present invention prepare a catalyst for the partial fluorination of HCFC-133a to HFC-134a having a catalytic form of $Cr_a L_b M_c O_x F_y$, it can significantly improve the stability of the catalyst.

When the catalyst of the present invention is used to produce HFC-134a, it is unnecessary to supply oxygen which is required to slow down the rapid inactivation of catalysts in conventional HFC-134a production. Furthermore, no supply of oxygen to the reactants can bring about a great reduction in the generation of by-products. Accordingly, the separation of HFC-134a from a mixture of the products of the catalytic reaction can be carried out in ease.

In addition, since no oxygen is supplied, unnecessary oxidation of HCl does not occur and only a very small amount of water is present in the system, which results in lowering the corrosion rate of the equipment used in the fluorination.

The preferred embodiments of the present invention will now be further described with reference to specific examples.

The catalyst of the present invention is superior in the change rate and in the selectivity. In addition, the change rate of the catalyst is maintained even after being used for a long period of time.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

EXAMPLE 1.

Preparation of the Catalyst 690 g of chromium hydroxide ($Cr(OH)_3 \cdot H_2O$), 2,030 g of $MgCl_2 \cdot 6H_2O$ and 15.5 g of $CeCl_3$ were mixed with 1L of water in such a way to make the weight ratio of Cr:Mg:Ce 1:1:0.02. To this solution, 1 L of an aqueous 48% HF solution was added and then, the reaction proceeded at 80° C. for 1 hour, and afterwards the product was filtered and dried. Thereafter, the dried product was sintered at 400° C. for 5 hours and then formed into a cylindrical pellet with a size of 4 mm×4 mm.

EXAMPLES 2–7.

Preparation of the Catalysts

Catalysts were prepared in a manner similar to that of Example 1, except that the compositions and their weight ratios were as shown in the following Table 1.

TABLE 1

| | Composition of the Catalysts |
|---|---|
| Example No. | Composition of Catalyst (weight ratio) |
| 1 | Cr:Mg:Ce = 1:1:0.02 |
| 2 | Cr:Mg:Ce = 1:0.3:0.05 |
| 3 | Cr:Mg:Ni = 1:4:0.02 |
| 4 | Cr:Ca:Ce = 1:1:0.02 |

TABLE 1-continued

| | Composition of the Catalysts |
|---|---|
| Example No. | Composition of Catalyst (weight ratio) |
| 5 | Cr:Mg:Zn = 1:2:0.05 |
| 6 | Cr:Mg:Al = 1:0.5:0.02 |
| 7 | Cr:Ca:Zn = 1:0.5:0.02 |

EXAMPLE 8.

Production of HFC-134a 50 g of the pelletized catalyst prepared in Example 1 was charged in a cylindrical reactor having a diameter of 2.54 cm and a length of 30 cm made by Inconel-600 tube (trade name), and slowly heated up to 400° C. with nitrogen being supplied at a rate of 50 ml/min, so as to remove trace water therefrom.

The reactor was cooled to 200° C. and HF was passed through it. During passing the HF, the reactor was heated to 375° C. and HCFC-133a was supplied to it in such an amount as to make the mole ratio of HCFC-133a to HF 1:8. The contact time of HF with HCFC-133a was 15 seconds. After being passed through a preheated region heated to 200° C., HF and HCFC-133a were introduced to the reactor.

For quantitative supply of HF and HCFC-133a, a mass velocity controller and a manometer were employed. Meanwhile, a gas chromatograph equipped with a Porapak N column was used to analyze the product.

The product having passed through the reactor was washed with a MgO suspension and water to remove HF and HCl therefrom and then dried with $CaCl_2$. The dried product was cooled to −60° C. to collect HFC-134a.

As a result of test for the HFC-134a production, it was measured that the change rate of HCFC-133a and the selectivity for HFC-134a were 25.8% and 97.8%, respectively.

EXAMPLES 9-15.

Production of HFC-134a

A number of HFC-134a production methods were carried out in a manner similar to that of Example 8, except that the catalysts prepared in Examples 2 to 7 were used, respectively, and that the reaction temperatures, the mole ratios of HF/HCFC-133a and the contact times were as shown in the Table 2.

The change rates of HCFC-133a and the selectivities for HFC-134a are given as shown in the following Table 2.

TABLE 2

| Exam. No. | Catalyst Source | React. Temp. (°C.) | Mol Ratio HF/ HCFC-133a | Contact Time (sec) | Change rate HCFC-133a | Select. HFC-134a |
|---|---|---|---|---|---|---|
| 8 | Exam. 1 | 375 | 8 | 15 | 25.8 | 97.8 |
| 9 | Exam. 2 | 380 | 10 | 1 | 27.2 | 99 |
| 10 | Exam. 3 | 375 | 5 | 60 | 19.4 | 98 |
| 11 | Exam. 4 | 370 | 15 | 30 | 29.4 | 98 |
| 12 | Exam. 5 | 390 | 15 | 30 | 30.6 | 99 |
| 13 | Exam. 6 | 380 | 20 | 10 | 33.2 | 99 |
| 14 | Exam. 7 | 370 | 8 | 10 | 24.8 | 98 |

EXAMPLE 15.

Measurement of Catalyst Deactivation

To ascertain the deactivation of the catalyst when it is used for a long period of time without supply of oxygen, the change rate of HCFC-133a was measured under the same conditions as Example 8. The result of the measurements showed a change rate of 24.5% after 720 hours.

What is claimed is:

1. A method for preparing a catalyst for the production of 1,1,1,2-tetrafluoroethane, comprising the steps of:

producing an admixture of a composition comprising chromium hydroxide hydrate and magnesium chloride or calcium chloride in a weight ratio of Cr to Mg or Ca ranging from 1:0.3 to 1:10 with an aqueous metal salt solution selected from the group consisting of cerium chloride, zinc chloride, nickel chloride, and aluminum chloride;

reacting the admixture in the liquid phase with an aqueous HF solution to give a paste; and sintering the paste.

2. The method in accordance with claim 1, wherein said composition comprises chromium hydroxide hydrate and a chloride of magnesium or calcium in a weight ratio of Cr to Mg or Ca ranging from 1:1 to 1:4.

3. The method in accordance with claim 1, wherein said metal salt is selected from a group consisting of cerium chloride, zinc chloride, nickel chloride and aluminum chloride.

4. The method in accordance with claim 1, wherein said metal salt content is in an amount of 5% by weight based on the weight of Cr.

5. The method in accordance with claim 1, wherein said aqueous HF solution is a 30 to 50% aqueous HF solution.

6. A catalyst for the production of 1,1,1,2-tetrafluoroethane represented as $Cr_aL_bM_cO_xF_y$;

wherein L is Mg or Ca; M is one element selected from a group consisting of Ce, Ni, Zn, and Al; and each value of a, b, c, x and y are all between 0 and 2.

* * * * *